United States Patent
Kitano et al.

(10) Patent No.: US 11,221,326 B2
(45) Date of Patent: Jan. 11, 2022

(54) METHOD OF PREPARING CELLS EXHIBITING DRUG RESISTANCE, METHOD OF SCREENING ANTICANCER DRUGS, AND ANTICANCER DRUG SCREENING KIT

(71) Applicant: TOPPAN PRINTING CO., LTD., Taito-ku (JP)

(72) Inventors: Shiro Kitano, Taito-ku (JP); Kei Tsukamoto, Taito-ku (JP); Shinji Irie, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 463 days.

(21) Appl. No.: 16/164,914

(22) Filed: Oct. 19, 2018

(65) Prior Publication Data

US 2019/0049431 A1 Feb. 14, 2019

Related U.S. Application Data

(63) Continuation of application No. PCT/JP2017/015806, filed on Apr. 19, 2017.

(30) Foreign Application Priority Data

Apr. 19, 2016 (JP) .............................. JP2016-083952
Apr. 19, 2016 (JP) .............................. JP2016-083953

(51) Int. Cl.
*C12P 1/00* (2006.01)
*G01N 33/50* (2006.01)

(52) U.S. Cl.
CPC ................................ *G01N 33/5011* (2013.01)

(58) Field of Classification Search
CPC ................................................ G01N 33/5011
See application file for complete search history.

(56) References Cited

PUBLICATIONS

Ochiai, "Novel mechanisms of drug resistance in cancer", Biochemistry, vol. 82, No. 1 pp. 34-38, 2010.
Takahashi, R., et al., "Loss of microRNA-27b contributes to breast cancer stem cell generation by activating ENPP1", Nature Communications, 6:7318, DOI: 10.1038/ncomms8318, pp. 1-15, 2015.
Chen, et al., "Exosomes from Drug-Resistant Breast Cancer Cells Transmit Chemoresistance by a Horizontal Transfer of MicroRNAs", PLOS ONE, vol. 9, Issue 4, e95240, 2014, 12 pages.
Mao, et al., "Exosomes decrease sensitivity of breast cancer cells to adriamycin by delivering microRNAs", Tumor Biol. (2016) 37:5247-5256, DOI 10.1007/s13277-015-4402-2, 10 pages.
International Search Report dated Jul. 25, 2017 in PCT/JP2017/015806, filed Apr. 19, 2017, 5 pages.
Chen WX. et al., "Exosomes from Drug-Resistant Breast Cancer Cells Transmit Chemoresistance by a Horizontal Transfer of MicroRNAs", PLOS ONE, 2014, vol. 9, No. 4, e95240, 12 pages.
Chen WX. et al., "Exosomes from docetaxel-resistant breast cancer cells alter chemosensitivity by delivering microRNAs", Tumor Biol., 2014, vol. 35, p. 9649-9659.
Ji R. et al., "Exosomes derived from human mesenchymal stem cells confer drug resistance in gastric cancer", Cell Cycle, 2015, vol. 14, No. 15, p. 2473-2483.
Corcoran C. et al., "Docetaxel-Resistance in Prostate Cancer: Evaluating Associated Phenotypic Changes and Potential for Resistance Transfer via Exosomes", PLOS ONE, 2012, vol. 7, No. 12, e50999, 12 pages.
Manabu Mikamori et al., "Suigan Saibo Kabu ni Okeru Exosome o Kaishita Yakuzai Taisei Kakutoku Kiko no Kaimei", 2015, Dai 115 Kai Annual Congress of Japan Surgical Society, OP-239-4, 1 page.

*Primary Examiner* — Albert M Navarro
(74) *Attorney, Agent, or Firm* — Oblon, McClelland, Maier & Neustadt, L.L.P.

(57) ABSTRACT

A method of producing drug resistant cells including contacting exosomes from a living organism exhibiting drug resistance with cells exhibiting no drug resistance such that drug resistant cells are formed, and culturing the drug resistant cells.

13 Claims, 1 Drawing Sheet

METHOD OF PREPARING CELLS EXHIBITING DRUG RESISTANCE, METHOD OF SCREENING ANTICANCER DRUGS, AND ANTICANCER DRUG SCREENING KIT

CROSS-REFERENCE TO RELATED APPLICATIONS

The present application is a continuation of International Application No. PCT/JP2017/015806, filed Apr. 19, 2017, which is based upon and claims the benefits of priority to Japanese Application No. 2016-083952, filed Apr. 19, 2016, and Japanese Application No. 2016-083953, filed Apr. 19, 2016. The entire contents of all of the above applications are incorporated herein by reference.

BACKGROUND OF THE INVENTION

Field of the Invention

The present invention relates to a method of preparing cells exhibiting drug resistance, a method of screening anticancer drugs, and an anticancer drug screening kit.

Discussion of the Background

Cells exhibiting drug resistance are chiefly used in innovative drug development fields such as of new drug development or drug repositioning screening. Dominant methods of preparing cells exhibiting drug resistance include a method of screening cells, or a method that uses cells whose nucleic acid has been edited using a genetic engineering technique. The latter method, which includes genome editing techniques, such as CRISPR/Cas 9 or GENESIS (registered trademark), attracting attention in recent years, has made it relatively easy to prepare cells exhibiting drug resistance. Another method may be a technique for preparing cells having drug resistance by adding a drug to target cells at a concentration not killing them, and culturing these cells over a long period.

Moreover, it is reported that microRNAs (miRNAs) or the like are important factors in the acquisition of drug resistance. It is reported that research comparing the expression levels of miRNAs in the presence or absence of drug resistance has been conducted and that some drugs relating to acquisition of drug resistance are in the process of being identified and, in a method, these drugs are added to cells to prepare cells exhibiting drug resistance (e.g., refer to Non-Patent Literatures 1 and 2).

Further, extracellular secretory membrane vesicles (exosomes) have been attracting attention as substances deeply involved in various phases of diseases such as cancers exhibiting drug resistance, the phases including onset, malignancy, progression, and metastasis. Thus, research of exosomes is actively underway in recent years. It is considered that exosomes contain nucleic acids such as miRNAs or mRNAs, or protein, and play a role of transfer means for propagation and transport (e.g., refer to Non-Patent Literature 3). As a specific example, there is a report on miRNAs derived from exosomes associated with resistance to Doxorubicin which is a drug for breast cancer (e.g., refer to Non-Patent Literatures 3 and 4). For example, there are reports, though only a few, that when exosomes derived from established cancer cell lines having drug resistance are added to the parent strain, the drug resistance is propagated to the parent strain. However, it is yet to be reported that the type of the cells which provide exosomes is different from the type of the cells which are imparted with drug resistance by the exosomes.

The greatest hurdle of cancer medical care is drug resistance. It has been reported that, generally, the drug resistance mechanism develops drug resistance due to a genetic mutation occurring in a gatekeeper or the like of a protein as a molecular target. However, resistance gene mutations obtained from drug-resistant tumors are extremely small in the amount, and thus it is difficult to believe that genetic mutation is introduced to all the tissues exhibiting drug resistance.

Non-Patent Literature 1: Takahiro O., "Novel mechanisms of drug resistance in cancer", Biochemistry, Vol. 82, No. 1 pp. 34-38, 2010.

Non-Patent Literature 2: Takahashi, R., et al., "Loss of microRNA-27b contributes to breast cancer stem cell generation by activating ENPP1", nature communications, DOI: 10.1038, pp. 1-15, 2015.

Non-Patent Literature 3: Wei-Xian C., et al, "Exosomes from Drug-Resistant Breast Cancer Cells Transmit Chemoresistance by a Horizontal Transfer of MicroRNAs", PLOS, Vol. 9, Issue 4, 2014.

Non-Patent Literature 4: Ling M., et al., "Exosomes decrease sensitivity of breast cancer cells to Adriamycin by delivering microRNAs", Tumor Biol., DOI 10.1007/s13277-015-4402-2, 2015.

SUMMARY OF THE INVENTION

According to an aspect of the present invention, a method of producing drug resistant cells includes contacting exosomes from a living organism exhibiting drug resistance with cells exhibiting no drug resistance such that drug resistant cells are formed, and culturing the drug resistant cells.

According to another aspect of the present invention, a kit for screening anticancer drugs includes exosomes from a living organism exhibiting drug resistance, and cancer cells exhibiting no drug resistance.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

The embodiments will now be described with reference to the accompanying drawings, wherein like reference numerals designate corresponding or identical elements throughout the various drawings.

<<Method of Preparing Cells Exhibiting Drug Resistance>>

A method of preparing cells exhibiting drug resistance (preparation method, manufacturing method) according to a first embodiment of the present invention includes bringing exosomes derived from a living organism exhibiting drug resistance, into contact with cells exhibiting no drug resistance, and culturing these cells (culturing step).

According to the preparation method of the present embodiment, cells exhibiting drug resistance can be obtained quickly and simply. Furthermore, the cells exhibiting drug resistance obtained by the preparation method of the present embodiment can be applied to new drug development, assessment in drug repositioning, selection and assessment of medical treatment, resolution and research for the mechanism of acquiring drug resistance, and the like.

Generally, the term drug resistance refers to a phenomenon that an organism has resistance to drugs that should exert some effects on the organism, disabling these drugs or making them unlikely to be effective.

Further, in the specification, the term drug refers to, but is not specifically limited to, a chemical substance which kills pathogenic microorganisms, such as bacteria or viruses, or cancer cells (malignant neoplasms), or which reduces or prevents growth of these microorganisms and neoplasms. Examples of the drug include, but are not limited to, antiviral drugs, antifungal drugs, antiprotozoal drugs, anticancer drugs, and the like.

In the present embodiment, the drug against which resistance is acquired is not specifically limited, but may preferably be an anticancer drug, or a drug which is administered in combination with the anticancer drug in cancer treatment. The drug is preferably an inhibitor for a tyrosine kinase, such as RAS, EGFR, BRAF, PIK3CA, ALK or ABL. Specifically, examples of the tyrosine kinase inhibitor include Cetuximab, Gefitinib, Erlotinib, Crizotinib, and the like.

Resistance to these tyrosine kinase inhibitors is produced, generally, by introducing a mutation for causing these tyrosine kinase genes to acquire resistance. However, as will be shown in an example described later, in the present embodiment, exosomes derived from a living organism are used for acquiring resistance. Specifically, the exosomes are derived from a living organism to which tyrosine kinase inhibitor resistance has been imparted by introduction of a mutation into these tyrosine kinase genes. The exosomes derived from the living organism are brought into contact with cells exhibiting no drug resistance to make them acquire drug resistance, without the need of introducing a genetic mutation into tyrosine kinase genes.

A preparation method according to the present embodiment will be described in detail below.

<Culturing Step>

First, the cells exhibiting no drug resistance are seeded and cultured in a cell culture vessel.

Examples of the cell culture vessel used in the culturing step include, but are not limited to, dishes, cell culture inserts (e.g., Transwell (registered trademark) insert, Netwell (registered trademark) insert, Falcon (registered trademark) cell culture insert, Millicell (registered trademark) cell culture insert, and the like), tubes, flasks, bottles, plates, and the like.

Cells exhibiting no drug resistance to be used are not specifically limited, but may be cells to which drug resistance is desired to be imparted. Examples of the cells include, but are not limited to, reproductive cells (spermatozoa, ova, and the like), somatic cells constituting a living body, stem cells, progenitor cells, cancer cells separated from a living body, cells separated from a living body and acquired immortalizing ability for stable in vitro retention (cell lines), cells separated from a living body for artificial genetic engineering, cells separated from a living body for artificial nucleus change, and the like.

Examples of the somatic cells constituting a living body include, but are not limited to, cells collected from any tissue such as skin, kidney, spleen, adrenal gland, liver, lung, ovarian, pancreatic, uterine, stomach, colon, small intestine, large intestine, bladder, prostate, testes, thymus, muscle, connective tissue, skeletal, cartilage, vascular tissue, blood, heart, eye, brain, nerve tissue, and the like. More specifically, examples of the somatic cells include, but are not limited to, fibroblasts, bone marrow cells, immune cells (e.g., B-lymphocytes, T-lymphocytes, neutrophils, macrophages, monocytes, and the like), red blood cells, platelets, osteocytes, bone marrow cells, pericytes, dendritic cells, keratinocytes, adipocytes, mesenchymal cells, epithelial cells, epidermal cells, endothelial cells, vascular endothelial cells, lymphatic endothelial cells, liver cells, pancreatic islet cells (e.g., α cells, β cells, δ cells, ε cells, PP cells, and the like), cartilage cells, cumulus cells, glial cells, neural cells (neuron), oligodendrocytes, microglia, astrocytes, heart cells, esophagus cells, skeletal muscle cells (e.g., smooth muscle cells, skeletal muscle cells, and the like), melanocytes, mononuclear cells, and the like.

Stem cells refer to cells having both an ability to replicate themselves, and an ability to differentiate into a plurality of other lineages. Examples of the stem cells include, but are not limited to, embryonic stem cells (ES cells), embryonic tumor cells, embryonic reproductive stem cells, induced pluripotent stem cells (iPS cells), neural stem cells, hematopoietic stem cells, mesenchymal stem cells, liver stem cells, pancreatic stem cells, muscle stem cells, reproductive stem cells, intestinal stem cells, cancer stem cells, hair follicle stem cells, and the like.

The precursor cells refer to cells that are in the process of differentiating into particular somatic cells or reproductive cells from the stem cells.

The cancer cells refer to cells that are derived from somatic cells and have acquired infinite proliferative capacity. Examples of cancers from which the cancer cells are derived include, but are not limited to, breast cancer (e.g., invasive ductal carcinoma, ductal carcinoma in situ, inflammatory breast cancer, etc.), prostate cancer (e.g., hormone dependent prostate cancer, non-hormone dependent prostate cancer, etc.), pancreatic cancer (e.g., pancreatic duct cancer, etc.), gastric cancer (e.g., papillary adenocarcinoma, mucinous adenocarcinoma, adenosquamous carcinoma, etc.), lung cancer (e.g., non-small cell lung cancer, small cell lung cancer, malignant mesothelioma, etc.), colon cancer (e.g., gastrointestinal stromal tumor, etc.), rectal cancer (e.g., gastrointestinal stromal tumor, etc.), large intestine cancer (e.g., familial colorectal cancer, hereditary nonpolyposis colorectal cancer, gastrointestinal stromal tumor, etc.), small intestine cancer (e.g., non-Hodgkin's lymphoma, gastrointestinal stromal tumor, etc.), esophagus cancer, duodenal cancer, tongue cancer, pharyngeal cancer (e.g., nasopharynx cancer, oropharynx cancer, hypopharyngeal cancer, etc.), head and neck cancer, salivary gland cancer, brain tumor (e.g., pineal astrocytoma, pilocytic astrocytoma, diffuse astrocytoma, anaplastic astrocytoma, etc.), neurinoma, liver cancer (e.g., primary liver cancer, extrahepatic bile duct cancer, etc.), kidney cancer (e.g., renal cell carcinoma, transitional cell carcinoma in pelvis renalis and urinary duct, etc.), gallbladder cancer, bile duct cancer, pancreatic cancer, hepatic cancer, endometrial cancer, endocervical cancer, ovarian cancer (e.g., ovarian epithelial carcinoma, extragonadal germ cell tumor, ovarian germ cell tumor, ovarian low malignant potential tumor, etc.), bladder cancer, urethral cancer, skin cancer (e.g., intraocular (ocular) melanoma, Merkel cell cancer, etc.), hemangiomas cancer, malignant lymphoma (e.g., reticulosarcoma, lymphosarcoma, Hodgkin's disease, etc.), melanoma (malignant melanoma), thyroid cancer (e.g., medullary thyroid carcinoma, etc.), parathyroid cancer, nasal sinus cancer, paranasal sinus cancer, bone tumor (e.g., osteosarcoma, Ewing's tumor, uterine sarcoma, soft tissue sarcoma, etc.), metastatic medulloblastoma, angiofibroma, dermatofibrosarcoma protuberans, retinoblastoma, penile cancer, testicular cancer, pediatric solid cancer (e.g., Wilms tumor, pediatric renal tumor, etc.), Kaposi's sarcoma, Kaposi's sarcoma caused by AIDS, maxillary sinus tumor, fibrous histiocytoma, leiomyosarcoma, rhandomyosarcoma, chronic myeloproliferative disease, leukemia (e.g., acute myelogenous leukemia, acute lymphoblastic leukemia, etc.), and the like.

The cell lines refer to cells that have acquired infinite proliferative capacity by an artificial operation in vitro. Examples of the cell lines include, but are not limited to, HCT116, Huh7, HEK293 (human embryonic kidney cells), HeLa (human cervical cancer cell lines), HepG2 (human liver cancer cell lines), UT7/TPO (human leukemia cell lines), CHO (Chinese hamster ovary cell lines), MDCK, MDBK, BHK, C-33A, HT-29, AE-1, 3D9, Ns0/1, Jurkat, NIH3T3, PC12, S2, Sf9, Sf21, High Five, Vero, and the like.

Subsequently, exosomes derived from a living organism exhibiting drug resistance are added, for contact with the cells exhibiting no drug resistance, followed by culturing. The exosomes may be brought into contact with the cells exhibiting no drug resistance using, for example, a method of mixing and adding purified exosomes or a composition containing exosomes to the culture medium, or other methods.

Generally, exosomes refer to membrane vesicles secreted by various cells and each having a diameter in the range of 40 nm to 150 nm. The membrane vesicles contain nucleic acids, such as miRNA and mRNA, protein, and lipid. In the preparation method of the present embodiment, these substances are taken to be involved in acquiring drug resistance.

The exosomes are secreted from almost all cells, and thus many body fluid samples contain exosomes. Therefore, the compositions containing the exosomes, which are derived from a living organism exhibiting drug resistance, are not specifically limited. Examples of such compositions include, but are not limited to, a body fluid sample collected from an animal exhibiting drug resistance, an extract of cells collected from an animal exhibiting drug resistance, a culture supernatant of cells collected from an animal exhibiting drug resistance, an extract of cultured cells exhibiting drug resistance, and a culture supernatant of cultured cells exhibiting drug resistance.

The drug resistance may be against one type of drug, or may be against two or more types of drugs.

In the present embodiment, the animal from which exosomes are derived is not specifically limited. Examples of the animal include, but are not limited to, humans, monkeys, dogs, cats, rabbits, pigs, cows, mice, rats, and the like. The kind of animal from which exosomes are derived can be arbitrarily selected depending on the purpose, or the like. The animal from which exosomes are derived is preferably a human. With the animal from which exosomes are derived being a human, the resultant cells can be applied to new drug development applicable to humans, assessment in drug repositioning, selection and assessment of medical treatment, resolution and research for the mechanism of drug resistance acquisition in humans, or the like.

In the present embodiment, the cultured cells from which exosomes are derived is not specifically limited, but may be cells exhibiting drug resistance. Examples of the cultured cells include cells similar to ones mentioned above as cells exhibiting no drug resistance. Of such cells, the cultured cells from which exosomes are derived are preferably neuronal cells, dendritic cells, immune cells, vascular endothelial cells, lymphatic endothelial cells, fibroblast cells, epithelial cells, myocardial cells, liver cells, pancreatic islet cells, smooth muscle cells, cancer cells, or cancer stem cells.

The type of cultured cells from which exosomes are derived may be the same as or may be different from the cells exhibiting no drug resistance i.e. targets to which drug resistance is imparted. In particular, when the cells exhibiting no drug resistance are cancer cells, the type of the cultured cells from which exosomes are derived may be the same as or may be different from the type of the cancer cells. Furthermore, the type of the cultured cells from which exosomes are derived is preferably different from the type of the cancer cells.

More specifically, examples of the body fluid sample, which is collected from an animal exhibiting drug resistance, include, but are not limited to, blood, serum, plasma, urine, buffy coat, saliva, semen, breast exudate, cerebrospinal fluid, tears, sputum, mucus, lymph fluid, ascites, pleural effusion, amniotic fluid, bladder lavage fluid, bronchoalveolar lavage fluid, and the like.

For example, tissues collected from an animal exhibiting drug resistance, or cultured cells exhibiting drug resistance may be co-cultured with the cells exhibiting no drug resistance, so that the exosomes derived from the tissues collected from an animal exhibiting drug resistance or the cultured cells exhibiting drug resistance are brought into contact with the cells exhibiting no drug resistance.

As a specific method for this purpose, for example, a two-stage culture vessel including an upper culture vessel with pores being provided to the bottom surface, and a lower culture vessel may be used. The pores of the upper culture vessel do not allow the tissues collected from an animal exhibiting drug resistance or the cultured cells exhibiting drug resistance to permeate, but allow the exosomes secreted from the tissues collected from an animal exhibiting drug resistance or secreted from the cultured cells to permeate. In this method, the upper culture vessel may be used for culturing the tissues collected from an animal exhibiting drug resistance or the cultured cells exhibiting drug resistance, while the lower culture vessel may be used for culturing the cells exhibiting no drug resistance, thereby bringing the exosomes secreted from the tissues collected from an animal exhibiting drug resistance or secreted from the cultured cells into contact with the cells exhibiting no drug resistance.

The exosomes may be ones obtained by recovering them from, concentrating, purifying, or isolating them from the samples mentioned above. Any of recovery, concentration, purification and isolation may be arbitrarily selected depending on the type and conditions of the samples mentioned above.

Any culture medium may be used as long as it is a base medium containing components (inorganic salts, carbohydrates, hormones, essential amino acids, non-essential amino acids, or vitamins) or the like necessary for the survival and growth of the cells. Thus, a culture medium can be appropriately selected depending on the kind of the cells. Examples of the culture medium include, but are not limited to, DMEM, Minimum Essential Medium (MEM), RPMI-1640, Basal Medium Eagle (BME), Dulbecco's Modified Eagle's medium: Nutrient Mixture F-12 (DMEM/F-12), or Glasgow Minimum Essential Medium (Glasgow MEM) may be used.

The culturing temperature is preferably in the range of 25° C. or more and 40° C. or less, more preferably 30° C. or more and 39° C. or less, and even more preferably 35° C. or more and 39° C. or less. The culturing environment may be arbitrarily set unless it directly affects preservation of the drugs, cells and tissues, and as long as it suitably retains the cell culture medium in use for an arbitrary period. A hydrodynamic flow, such as reflux, may be added as necessary unless the culturing environment is changed significantly. The culturing environment may be, for example, of approximately 5% $CO_2$.

The culturing time may be arbitrarily set depending on the origin and the amount of the liquid substance, and the like. The culturing time is, for example, preferably 12 hours or more, more preferably in the range of 12 hours or more and 96 hours or less, and even more preferably 24 hours or more and 72 hours or less.

The number of exosomes to be added may be arbitrarily set depending on the type and the number of cells exhibiting no drug resistance, and the like. The number of exosomes is, for example, preferably $1 \times 10^3$ or more, more preferably $1 \times 10^7$ or more, and even more preferably in the range of $1 \times 10^7$ or more and $1 \times 10^{12}$ or less, relative to $2 \times 10^4$ cells exhibiting no drug resistance.

<<Method of Screening Anticancer Drugs>>

A method of screening anticancer drugs according to a second embodiment of the present invention includes a drug resistance acquiring step of allowing cancer cells exhibiting no drug resistance to acquire drug resistance through the method according to the first embodiment (using the preparation method according to the first embodiment), followed by an anticancer drug addition step of bringing the cancer cells that have acquired drug resistance into contact with at least one type of anticancer drug to culture the cancer cells, and followed by an assessment step of calculating viability of the cancer cells to assess the anticancer drug.

In other words, the method of screening anticancer drugs according to the second embodiment of the present invention includes a drug resistance acquiring step of bringing exosomes derived from a living organism exhibiting drug resistance into contact with cancer cells exhibiting no drug resistance, culturing the cancer cells and allowing the cancer cells to acquire drug resistance, followed by an anticancer drug addition step of bringing the cancer cells that have acquired drug resistance into contact with at least one type of anticancer drug to culture the cancer cells, and followed by an assessment step of calculating viability of the cancer cells to assess the anticancer drug.

The screening method of the present embodiment enables more quick and simple assessment of anticancer drugs. Furthermore, the screening method of the present embodiment can be applied to new drug development, assessment in drug repositioning, selection and assessment of medical treatment, resolution and research for the mechanism of acquiring drug resistance, and the like.

The method of the present embodiment will be described in detail below.

<Drug Resistance Acquiring Step>

First, cancer cells exhibiting no drug resistance are seeded and cultured in a cell culture vessel. The cell culture vessel may be one similar to the vessels mentioned in "Method of preparing cells exhibiting drug resistance" of the first embodiment set forth above.

Cancer cells to be used are not specifically limited, but may be cells to which drug resistance is desired to be imparted. Cancers from which cancer cells are derived may be the cancer cells mentioned as the cells exhibiting no drug resistance in "Method of preparing cells exhibiting drug resistance" of the first embodiment set forth above. Of such cancers, the cancer from which cancer cells are derived is preferably metastatic medulloblastoma, gastrointestinal stromal tumor, dermatofibrosarcoma protuberans, colon cancer, rectal cancer, colorectal cancer, lung cancer, chronic myeloproliferative disease, acute myelogenous leukemia, thyroid cancer, pancreatic cancer, bladder cancer, kidney cancer, malignant melanoma, breast cancer, prostate cancer, ovarian cancer, cervical cancer, head and neck cancer, brain tumor, or liver cancer.

Subsequently, exosomes derived from a living organism exhibiting drug resistance are added to the cancer cells exhibiting no drug resistance for contact therewith, followed by culturing. The exosomes may be brought into contact with the cancer cells exhibiting no drug resistance using, for example, a method of mixing and adding purified exosomes or a composition containing exosomes to the culture medium, or other methods. The exosomes derived from a living organism exhibiting drug resistance and the composition containing exosomes may be ones similar to the exosomes derived from a living organism exhibiting drug resistance, and the body fluid sample collected from an animal exhibiting drug resistance, as mentioned in "Method of preparing cells exhibiting drug resistance" set forth above.

The body fluid sample is preferably one collected from a cancer patient exhibiting drug resistance. The type of cancer of the cancer patient is not specifically limited, but may be a cancer similar those mentioned as cancers from which the aforementioned cancer cells are derived. The type of cancer of the cancer patient may be the same as or may different from the type of cancer of the cancer cells.

Tissues collected from an animal exhibiting drug resistance, or cultured cells exhibiting drug resistance may be co-cultured with the cancer cells exhibiting no drug resistance, so that the exosomes derived from the tissues collected from an animal exhibiting drug resistance or the cultured cells exhibiting drug resistance are brought into contact with the cancer cells exhibiting no drug resistance.

As a specific method for this purpose, for example, a two-stage culture vessel including an upper culture vessel with pores being provided to the bottom surface, and a lower culture vessel may be used. The pores of the upper culture vessel do not allow the tissues collected from an animal exhibiting drug resistance or the cultured cells exhibiting drug resistance to permeate, but allow the exosomes secreted from the tissues collected from an animal exhibiting drug resistance or secreted from the cultured cells to permeate. In this method, the upper culture vessel may be used for culturing the tissues collected from an animal exhibiting drug resistance or the cultured cells exhibiting drug resistance, while the lower culture vessel may be used for culturing the cancer cells exhibiting no drug resistance, thereby bringing the exosomes secreted from the tissues collected from an animal exhibiting drug resistance or secreted from the cultured cells into contact with the cancer cells having no drug resistance.

In the drug resistance acquiring step, the cancer cells that have acquired drug resistance may be further co-cultured with at least one other type of cells, for use as a three-dimensionally organized cell structure. The cells which are co-cultured with the cancer cells that have acquired drug resistance are not specifically limited, but may be ones similar to the cells mentioned regarding cultured cells from which exosomes are derived. In particular, the cells which are co-cultured with the cancer cells that have acquired drug resistance are preferably ones selected from the group consisting of neuronal cells, dendritic cells, immune cells, vascular endothelial cells, lymphatic endothelial cells, fibroblast cells, epithelial cells, myocardial cells, liver cells, pancreatic islet cells, smooth muscle cells, cancer cells, and cancer stem cells.

A well-known preparation method may be used for the method of co-culturing the cancer cells that have acquired drug resistance with at least one type of cells, and preparing a three-dimensionally organized cell structure. Examples of the method of preparing the cell structure include the following methods.

Generally, a cell structure containing the cancer cells that have acquired drug resistance and at least one type of cells is formed in a cell culture vessel. The cell culture vessel is not specifically limited as long as it is one enabling formation of a cell structure, and culturing of the cell structure as formed. The cell culture vessel may be one similar to the vessels mentioned in "Method of preparing cells exhibiting drug resistance" of the first embodiment set forth above. When forming a cell structure for use in the present embodiment (may be termed cell structure of the present embodiment hereinafter), a dish or various cell culture inserts are preferably used because the resultant cell structure would enable more appropriate anticancer drug screening.

The cell structure of the present embodiment preferably includes cancer cells and cells (stromal cells) structuring stroma. Stroma is an important structure in a cancer microenvironment in vivo. In short, an environment of cancer cells in vivo can be reproduced by allowing a three-dimensional stroma cell structure to contain cancer cells. The anticancer activity of the anticancer drug can be more suitably assessed by using such a cell structure.

Examples of the stroma cells include endothelial cells, fibroblast cells, neuronal cells, dendritic cells, macrophages, mast cells, epithelial cells, myocardial cells, liver cells, pancreatic islet cells, tissue stem cells, smooth muscle cells, and the like. The type of stroma cells contained in the cell structure of the present embodiment may be one, or may be two or more.

A vascular network structure and a lymphatic network structure are important for the growth and activity of cancer cells. Therefore, the cell structure of the present embodiment preferably includes a vascular network structure. Namely, the cell structure of the present embodiment is preferably one in which a vascular network structure such as of lymphatic vessels and/or blood vessels is three-dimensionally formed inside a laminate of non-vascularized cells to form tissues closer in structure to those in vivo. The vascular network structure may be formed only on the inside of the cell structure, or may be formed so that at least part thereof is exposed on the front surface or the bottom surface of the cell structure. In the present embodiment and the present specification, the expression "vascular network structure" refers to a network structure, such as a blood vessel network or a lymphatic vessel network, in living tissues.

The vascular network structure can be formed so as to contain endothelial cells constituting blood vessels, as stroma cells. The endothelial cells contained in the cell structure of the present embodiment may be vascular endothelial cells, or may be lymphatic endothelial cells. Alternatively, the cell structure may contain both the vascular endothelial cells and the lymphatic endothelial cells.

Any cell structure may be used in the present embodiment as long as it is a structure formed of multi-layered cells. Also, the method of forming the structure is not specifically limited. For example, the method may be one forming layers one by one and laminating them in sequence, or may be one concurrently forming two or more cell layers, or may be one forming a multi-layered cell layer by appropriately combining both of the former methods. Further, the cell structure of the present embodiment may be a multi-layered structure in which the cell types constituting the respective cell layers may be different between the layers, or may be a cell structure in which the cell types constituting the respective cell layers are common to all the layers of the structure. For example, the method may be one forming a layer for each cell type and laminating the cell layers in sequence, or may be one preparing a cell mixture solution beforehand by mixing a plurality of types of cells and forming a cell structure having a multilayer structure from the cell mixture solution.

Examples of the method of forming layers one by one and laminating them in sequence include one described in JP 4919464 B, i.e., one continuously laminating cell layers by alternating a step of forming a cell layer with a step of bringing the formed cell layer into contact with a solution containing components of an extracellular matrix (ECM). For example, when performing this method, a cell mixture in which all the cells forming a cell structure are mixed is prepared beforehand, and then individual cell layers are formed using this cell mixture, thereby producing a cell structure in which a vascular network structure is formed over the entire structure. Further, by forming each cell layer for each cell type, a cell structure is formed in which a vascular network structure is formed only in the layer formed of endothelial cells.

Examples of the method of concurrently forming two or more cell layers include one described in JP 5850419 B, i.e., one applying a material, which contains a polymer containing an arginine-glycine-aspartic acid (RGD) sequence bound with integrin and a polymer interacting with the polymer containing the RGD sequence, to the overall surfaces of cells beforehand, and accommodating the cells coated with this adhesive membrane in a cell culture vessel, followed by accumulating the coated cells by centrifugation treatment or the like, thereby forming a cell structure formed of a multi-layered cell layer. For example, when performing this method, a cell mixture is prepared beforehand by mixing all the cells forming a cell structure, and then coated cells are prepared by adding an adhesive component to the cell mixture, followed by one centrifugation, thereby producing a cell structure in which a vascular network structure is formed over the entire structure. Furthermore, for example, cells coated with endothelial cells and cells coated with fibroblast cells are separately prepared. Then a multilayer formed of the cells coated with fibroblast cells is formed. Then, a layer formed of the cells coated with endothelial cells is laminated on the multilayer formed of the cells coated with fibroblast cells, followed by further laminating thereon another multilayer formed of the cells coated with fibroblast cells, thereby forming a thick cell structure including a vascular network structure sandwiched between the fibroblast cell layers.

The number of cell layers forming a cell structure is measured by dividing the total number of cells forming a three-dimensional structure by the number of cells per one layer (the number of cells necessary to form one layer). The number of cells per one layer can be checked by planarly culturing cells beforehand in a cell vessel to be used for forming the cell structure such that the cells become confluent. Specifically, the number of cell layers of a cell structure formed in such a cell vessel can be calculated by measuring the total number of cells forming the cell structure, and dividing the total number by the number of cells per one layer in the cell vessel.

The cell structure of the present embodiment can be formed by a method including the following steps (a) to (c).
  (a) A step of mixing cells with an extracellular matrix component in a cationic buffer solution to obtain a mixture;
  (b) A step of seeding the mixture obtained in step (a) in a cell culture vessel; and
  (c) A step of removing liquid components from the cell mixture in the cell culture vessel after step (b), and obtaining a cell structure in which cells are multi-layered in the cell culture vessel.

In step (a) of the present embodiment, a three-dimensional cell tissues having only a few large voids on the inside can be obtained by mixing the cells with a buffer solution (cationic buffer solution) containing cationic substance and an extracellular matrix component, and forming a cell aggregate from the cell mixture. Further, the obtained three-dimensional cell tissues, which are comparatively stable, can be cultured for at least several days, and are unlikely to be damaged during medium replacement.

Step (b) of the present embodiment may include precipitating the cell mixture seeded in the cell culture vessel into the cell culture vessel. The cell mixture may be actively precipitated into the cells by centrifugation or the like, or may be naturally precipitated.

In Step (a), the cells are preferably further mixed with a strong electrolytic polymer. If the cells are mixed with a cationic substance, a strong electrolytic polymer and an extracellular matrix component, even natural precipitation can achieve thick three-dimensional cell tissues with fewer voids therein, without requiring a treatment, such as centrifugation, of actively accumulating cells in step (b).

Examples of the cationic buffer solution include tris-hydrochloric acid buffer solution, tris-maleic acid buffer solution, bis-tris buffer solution, HEPES, and the like. The concentration and pH of the cationic substance in a cationic buffer solution (e.g., tris in a tris-hydrochloric acid buffer solution) are not specifically limited as long as they do not adversely affect the growth of the cells and formation of the cell structure. For example, the concentration of the cationic substance in a cationic buffer solution may be in the range of 10 mM to 100 mM, preferably in the range of 40 mM to 70 mM, and more preferably 50 mM. The pH of a cationic buffer solution may be in the range of 6.0 to 8.0, preferably in the range of 6.8 to 7.8, and more preferably in the range of 7.2 to 7.6. Examples of the strong electrolytic polymer include, but are not limited to, glycosaminoglycans such as heparin, chondroitin sulfate (e.g., chondroitin 4-sulfate, or chondroitin 6-sulfate), heparan sulfate, dermatan sulfate, keratan sulfate, hyaluronic acid, and the like; dextran sulfate, rhamnan sulfate, fucoidan, carrageenan, polystyrene sulfonic acid, polyacrylamide-2-methylpropanesulfonic acid, polyacrylic acid, derivatives thereof, and the like. The strong electrolytic polymer may be mixed singly or in combination of two or more into the mixture prepared in step (a). In the formation of the cell structure of the present embodiment, the polymer electrolyte may preferably be a glycosaminoglycan. Further, at least one from among heparin, dextran sulfate, chondroitin sulfate, and dermatan sulfate may more preferably be used. The strong electrolytic polymer used in the present embodiment may more preferably be heparin.

The amount of the strong electrolytic polymer mixed in the cationic buffer solution is not specifically limited unless it adversely affects the growth of the cells and the formation of the cell structure. For example, the concentration of the strong electrolytic polymer in the cationic buffer solution may be in the range of higher than 0 mg/mL and lower than 1.0 mg/mL, preferably in the range of 0.025 mg/mL to 0.1 mg/mL, and more preferably in the range of 0.05 mg/mL to 0.1 mg/mL. Further, in the present embodiment, the mixture may be prepared without mixing the strong electrolyte, for formation of the cell structure.

Examples of the extracellular matrix component include collagen, laminin, fibronectin, vitronectin, elastin, tenascin, entactin, fibrillin, proteoglycan, modifications or variants thereof, and the like. Proteoglycan may be chondroitin sulfate proteoglycan, heparan sulfate proteoglycan, keratan sulfate proteoglycan, dermatan sulfate proteoglycan, or the like. The extracellular matrix component may be mixed singly or in combination of two or more into the mixture prepared in step (a). When forming the cell structure of the present embodiment, it is preferable to use collagen, laminin, or fibronectin, and it is more preferable to use collagen. As long as there is no adverse effect on the growth of the cells and the formation of the cell structure, modifications or variants of the extracellular matrix component mentioned above may be used. The amount of the extracellular matrix component to be mixed in the cationic buffer solution is not specifically limited unless it adversely affects the growth of the cells and the formation of the cell structure. For example, the concentration of the extracellular matrix component in the cationic buffer solution may be in the range of higher than 0 mg/mL and lower than 1.0 mg/mL, preferably in the range of 0.025 mg/mL to 0.1 mg/mL, and more preferably in the range of 0.05 mg/mL to 0.1 mg/mL.

The ratio of mixing the strong electrolytic polymer and the extracellular matrix component in the cationic buffer solution is in the range of 1:2 to 2:1. When forming the cell structure of the present embodiment, the ratio of mixing the strong electrolytic polymer and the extracellular matrix component is preferably in the range of 1:1.5 to 1.5:1, and more preferably 1:1.

Steps (a) to (c) described above are repeatedly performed to form a sufficiently thick cell structure. In the repetition, on the cell structure obtained in a previous iteration of step (c), the mixture prepared in step (a) is seeded, as step (b), followed by step (c) of this iteration. The cell composition of the mixture to be newly seeded on the cell structure obtained in step (c) may be the same as or may be different from the cell composition forming the cell structure that has already been formed.

In the repetition of steps (a) to (c), the obtained cell structure may be cultured after step (c) but before step (b). Culturing conditions, such as composition of the culture medium used in the culturing, culturing temperature, culturing time, and atmospheric composition during culturing, are determined so as to be suitable for culturing the cells forming the cell structure. Examples of the culture medium include D-MEM, E-MEM. MEMα, RPMI-1640, Ham's F-12, and the like.

Step (a) may be followed by a step (a'-1) of removing liquid from the obtained mixture to obtain cell aggregates, and a step (a'-2) of suspending the cell aggregates in a solution. Then, the process may proceed to step (b).

Alternatively, step (a) may be followed by steps (b'-1) and (b'-2) described below in place of step (b). In the present embodiment and the present specification, the term "cell viscous body" refers to gel-like cell aggregates as described in Non-Patent Literature 2.

The replacement steps are specifically:
A step (b'-1) of seeding the mixture obtained in step (a) in the cell culture vessel and then removing liquid components from the mixture to obtain a cell viscous body, and A step (b'-2) of suspending the cell viscous body in a solvent in a cell culture vessel.

Desired tissues can be obtained by performing steps (a) to (c) described above, but more homogenous tissues can be obtained by performing steps (a), (a'-1), (a'-2) and (b) in this order.

The solvent for preparing a cell suspension is not particularly limited unless it is toxic to the cells and unless it impairs the growth and functions of the cells. Thus, the cell suspension may be water, a buffer solution, a cell culture medium, or the like. Examples of the buffer solution include phosphate buffered saline (PBS), HEPES, Hanks buffer solution, and the like. The culture medium may be D-MEM, E-MEM, MEMα, RPMI-1640, Ham's F-12, or the like.

Step (c) may be replaced by step (c') of removing liquid components from the seeded mixture and forming a layer of cells on a base material.

The method of removing liquid components in steps (c) and (c') is not specifically limited, unless the method adversely affects the growth of the cells and the formation of the cell structure. Thus, a method known to skilled persons may be appropriately used as a method of removing liquid components from a suspension of liquid components and solid components. Examples of the method include centrifugation, magnetic separation, filtration, and the like. For example, when a cell culture insert is used as a cell culture vessel, the cell culture insert seeded with the mixture is centrifuged at 10° C. at 400×g for 1 minute, for removal of liquid components.

<Anticancer Drug Addition Step>

After the drug resistance acquiring step, at least one type of anticancer drug is brought into contact with the cancer cells that have acquired drug resistance, followed by culturing. Any method may be used for bringing the anticancer drug into contact with the cancer cells that have acquired drug resistance. For example, the anticancer drug may be mixed into the culture medium for contact with the cancer cells.

The type of anticancer drug is not specifically limited. Any anticancer drug may be used, including well-known anticancer drugs and novel compounds. The anticancer drug may be added singly or in combination of two or more. The amount of the anticancer drug to be added may be appropriately selected based on the type and the amount of the cancer cells.

The culture medium to be used, the culturing temperature, the culturing time, and the culturing environment are the same as those mentioned in the drug resistance acquiring step.

<Assessment Step>

After the anticancer drug administrating step, viability of the cancer cells is calculated to assess the anticancer drug.

A well-known method may be used as the method of calculating viability of the cancer cells. For example, the method may be one that uses a labeling substance to label the cancer cells beforehand to count the number of viable cells.

The counting of the number of viable cancer cells will be described in detail. Specifically, the number of viable cancer cells may be assessed using a signal correlated with the viable cancer cells or their abundance. It is not always necessary to count cancer cells when they are all alive, but the viable cancer cells at the time of assessment may only have to be counted. For example, cancer cells may be labeled so that they are distinguished from other cells, and the signal from the label may be checked as an indicator. For example, the cancer cells may be fluorescently labeled and then the cells may be determined as to whether they are alive or dead, so that the cancer cells which are alive in the cell structure can be directly counted. In this case, an image analysis technique may be used. Life or death of cells may be determined using a well-known method, such as trypan blue staining, PI (propidium iodide) staining, or the like. The fluorescent labeling of the cancer cells may be based on a known method such as an immunostaining method. For example, this method uses an antibody against a substance specifically expressed on the cell surfaces of cancer cells as a primary antibody, and a fluorescently-labeled secondary antibody specifically binding to the primary antibody. Life or death determination of the cells and measurement of the number of viable cells may be performed using the intact cell structure, or may be performed in a state where the cell structure is broken into individual cells. For example, the three-dimensional cell structure after labeling the cancer cells and the dead cells may be disrupted, and then only the cancer cells which are alive at the time of the assessment may be directly counted by fluorescence activated cell sorting (FACS) or the like using the label as an indicator.

Examples of the substance for labeling cancer cells include, but are not limited to, fluorochromes, fluorescent beads, quantum dots, biotin, antibodies, antigens, energy absorbing materials, radioisotopes, chemical luminescent materials, enzymes, and the like. Of these substances, fluorochromes are preferably used. Specifically, examples of the fluorochromes include FAM (carboxyfluorescein), JOE (6-carboxy-4',5'-dichloro-2',7'-dimethoxyfluorescein), FITC (fluorescein isothiocyanate), TET (tetrachlorofluorescein), HEX (5'-hexachloro-fluorescein-CE phosphoramidite), Cy3, Cy5, Alexa568, Alexa647, PKH26, PKH67GL, and the like.

If the viability of the cancer cells in the group, to which an anticancer drug has been added, is lower than the viability of the cancer cells in the group, to which an anticancer drug has not been added, it may be determined that the cancer cells have drug sensitivity to the anticancer drug, and the anticancer drug is effective against the cancer cells.

If the viability the cancer cells in the group, to which a non-anticancer drug has been added, is approximately the same or higher than the viability of the cancer cells in the group, to which an anticancer drug has not been added, it may be determined that the cancer cells have acquired drug resistance to the anticancer drug, and the anticancer drug is not effective against the cancer cells.

<<Anticancer Drug Screening Kit>>

An anticancer drug screening kit according to a third embodiment of the present invention includes a liquid substance derived from a living organism exhibiting drug resistance, and cancer cells exhibiting no drug resistance.

The kit of the present embodiment can assess an anticancer drug more quickly and simply. The kit of the present embodiment can be applied to new drug development, assessment in drug repositioning, selection and assessment of medical treatment, resolution and research for the mechanism of acquiring drug resistance, and the like. The kit of the present embodiment may further include a cell culture vessel.

When the kit includes a cell culture vessel, the kit may be in a state of being already provided with the cancer cells exhibiting no drug resistance, which have been cultured in the cell culture vessel. The cell culture vessel may be one similar to the vessels mentioned in "Method of screening anticancer drugs" of the second embodiment set forth above.

The kit of the present embodiment may further include a culture medium for culturing cancer cells, a substance for labeling the cancer cells, a detection device for calculating viability of the cancer cells, and the like.

The cell culture medium and the like may be similar to those which are mentioned in "Method of screening anticancer drugs" of the second embodiment set forth above. The detection device may be a microplate reader, fluorescence scanner, two-photon excitation scanner, fluorescence microscope, or the like.

EXAMPLES

The present invention will be described below by way of examples, but the present invention should not be limited to these examples.

<Example 1> Preparation of Resistant Lines Using Extracellular Secreted Membrane Vesicles Derived from Resistant Cell Line (1)

As a biological sample exhibiting drug resistance, a human colorectal adenocarcinoma cell line HCT116 (ATCC (registered trademark) CCL-247) exhibiting resistance to Cetuximab (Erbitux manufactured by Merck Serono) was used. As cells exhibiting no drug resistance, a human colorectal adenocarcinoma cell line HT29 (ATCC (registered trademark) HTB-38TM was used.

As a cell culture vessel, a Transwell cell culture insert (#3470 manufactured by Corning Incorporated) was used. The culture medium used was D-MEM (043-30085 manufactured by Wako Pure Chemical Corporation) containing 10 vol/vol % of bovine serum (EXO-FBS-50A-1 manufactured by System Biosciences, LLC), and 1 vol/vol % of penicillin-streptomycin (168-23191 manufactured by Wako Pure Chemical Corporation).

Cells exhibiting no drug resistance were subjected to fluorescent labeling (PKH67GL manufactured by SIGMA Corporation) in advance, and drug sensitivity was assessed through viable count analysis.

Drugs were each assessed three times using a final concentration of 1 mg/mL of Cetuximab (Erbitux manufactured by Merck Serono).

As exosomes derived from drug resistant cell line, ones recovered from the culture supernatant of human colorectal adenocarcinoma cell line HCT116 (ATCC (registered trademark) CCL-247) by ultracentrifugation were used. Assessments were conducted with respect to two conditions of 0 exosomes (Condition A) (no addition of the exosomes derived from the drug resistant cell line), and $1 \times 10^9$ exosomes (Condition B).

In viable count analysis, drug sensitivity was assessed by using a trypan blue solution and by counting cells in the fluorescence mode of a cell counter (Countess II) manufactured by Life Technologies Inc.

Viable count analysis will be described in detail as follows.

First, an appropriate amount of a Tris buffer solution (50 mM, pH 7.4) is added to the Transwell cell culture insert, and then, the liquid components are removed. This series of steps is performed three times. Next, 300 µL of 0.25% trypsin-EDTA solution (manufactured by Invitrogen Corporation) is added to the Transwell cell culture insert and incubated in a $CO_2$ incubator (37° C., 5% $CO_2$) for 15 minutes. Then, the entire solution is recovered and transferred to a 1.5-mL recovery tube in which 300 µL of 0.25% trypsin-EDTA solution (manufactured by Invitrogen Corporation) has been added beforehand. Next, 100 µL, of 0.25% trypsin-EDTA solution (manufactured by Invitrogen Corporation) is added to the Transwell cell culture insert and incubated in a $CO_2$ incubator (37° C., 5% $CO_2$) for 5 minutes together with the 1.5-mL recovery tube. Then, the entire solution is recovered and transferred to the 1.5-mL recovery tube, followed by further adding 300 µL of 0.25% trypsin-EDTA solution (manufactured by Invitrogen Corporation) and incubation in a $CO_2$ incubator (37° C., 5% $CO_2$) for 5 minutes, thereby obtaining a cell structure dispersion.

The cell structure dispersion is immersed in the trypan blue to count viable cells in the fluorescence mode of a cell counter (Countess II) manufactured by Life Technologies Corp. to assess the viable count.

In the drug sensitivity assessment, CNT (cell viability) %=(viable count with addition of drug)/(viable count with addition of no drug)×100(%) is used as an assessment value.

As comparison, drug sensitivity is also assessed for Conditions C and D. Condition C is the case of adding the exosomes derived from the serum of a healthy person, and Condition D is the case of using a biological sample (HCT116) exhibiting drug resistance.

The detailed procedure is as shown below.
<1> Seeding and Culturing of Cell Line Exhibiting No Drug Resistance
  (1) $2 \times 10^4$ HT29 cells were seeded in a Transwell cell culture insert.
  (2) An appropriate amount of culture medium was added to the Transwell cell culture insert, followed by culturing in a $CO_2$ incubator (37° C., 5% $CO_2$) for 24 hours.
<2> Co-Culturing of Exosomes
  (1) An appropriate amount of culture medium was mixed with exosomes so as to satisfy Conditions A to D.
  (2) The mixture was added to the Transwell cell culture insert, followed by culturing in a $CO_2$ incubator (37° C., 5% $CO_2$) for 24 to 96 hours.
<3> Addition of Drug
  (1) An appropriate amount of culture medium was mixed with a drug so as to have a final concentration of 1 mg/mL.
  (2) The mixture was added to the Transwell cell culture insert, followed by culturing in a $CO_2$ incubator (37° C., 5% $CO_2$) for 72 hours.
<4> Drug Sensitivity Assessment
  (1) Viable cell counts resulting from Conditions A to D were analyzed using the method mentioned above to assess drug sensitivity. The results are shown in FIG. 1.

Figure 1:
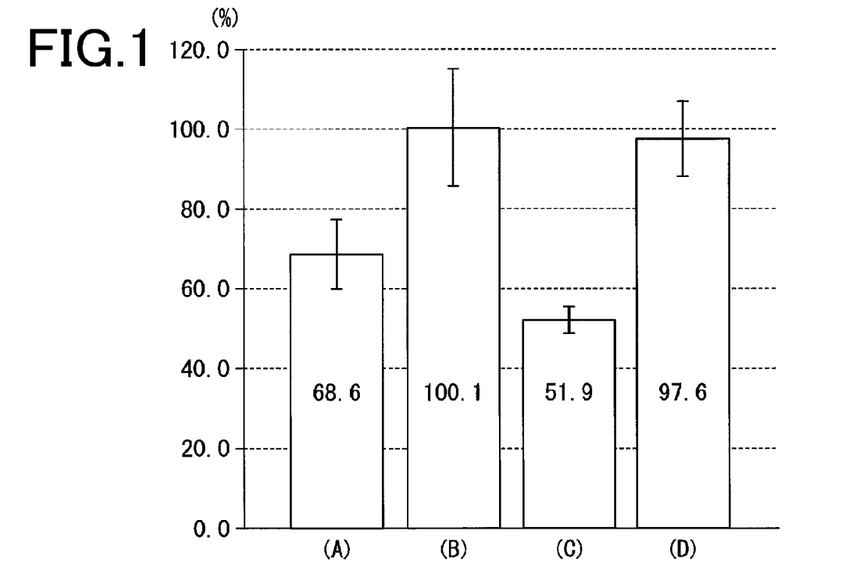
FIG. 1 is a graph showing assessment of drug sensitivity under Conditions A to D of Example 1.

As shown in FIG. 1, the cells to which $1 \times 10^9$ exosomes (Condition B) were added had predominantly higher CNT % than the cells to which 0 exosomes (Condition A) were added (cells having no addition of the exosomes derived from a drug resistant cell line), thus indicating acquisition of drug resistance.

Further, the cells to which $1 \times 10^9$ exosomes (Condition B) were added had results substantially similar to those of the cells to which the biological sample exhibiting drug resistance (Condition D) was added. In the case of using the exosomes derived from the serum of a healthy person (Condition C), conversely, results indicating more effectiveness were obtained.

The HT29 cells of Condition B that had acquired drug resistance were searched for KRAS mutation by use of digital PCR, but KRAS genetic mutation of allowing acquisition of Cetuximab resistance was not found.

<Example 2> Preparation of Resistant Lines Using Extracellular Secreted Membrane Vesicles Derived from Resistant Cell Line (2)

As a biological sample exhibiting drug resistance, a human alveolar basal epithelial cell line A549 (ATCC (registered trademark) CCL-185) exhibiting resistance to Cetuximab (Erbitux manufactured by Merck Serono) was used. As cells exhibiting no drug resistance, a human colorectal adenocarcinoma cell line HT29 (ATCC (registered trademark) HTB-38TM was used.

As a cell culture vessel, a Transwell cell culture insert (#3470 manufactured by Corning Incorporated) was used. The culture medium used was D-MEM (043-30085 manufactured by Wako Pure Chemical Corporation) containing 10 vol/vol % of bovine serum with non-extracellular secreted vesicles (EXO-FBS-50A-1 manufactured by System Biosciences, LLC), and 1 vol/vol % of penicillin-streptomycin (168-23191 manufactured by Wako Pure Chemical Corporation).

Cells exhibiting no drug resistance were subjected to fluorescent labeling (PKH67GL manufactured by SIGMA Corporation) in advance, and drug sensitivity was assessed through viable count analysis.

Drugs were each assessed three times using a final concentration of 1 mg/mL of Cetuximab (Erbitux manufactured by Merck Serono).

As exosomes derived from drug resistant cell line, a sample (exosomes) recovered from the culture supernatant of a human alveolar basal epithelial cell line A549 (ATCC (registered trademark) CCL-185) by ultracentrifugation were used. Assessments were conducted with respect to three conditions of 0 exosomes (Condition A) (no addition of the exosomes derived from the drug resistant cell line), $1 \times 10^8$ exosomes (Condition F), and $1 \times 10^9$ exosomes (Condition G).

In viable count analysis, drug sensitivity was assessed, as in Example 1, by using a trypan blue solution and by counting cells in the fluorescence mode of a cell counter (Countess II) manufactured by Life Technologies Inc.

In the drug sensitivity assessment, CNT %=(viable count with addition of drug under the conditions mentioned above)/(viable count with addition of no drug)×100(%) was used as an assessment value.

As comparison, drug sensitivity was also assessed for Conditions C and H. Condition C was the case of adding the exosomes derived from the serum of a healthy person, and Condition H was the case of using a biological sample exhibiting drug resistance.

In the specific procedure, methods as in [1] to [4] of Example 1 were used. The results are shown in FIG. 2.

Figure 2:
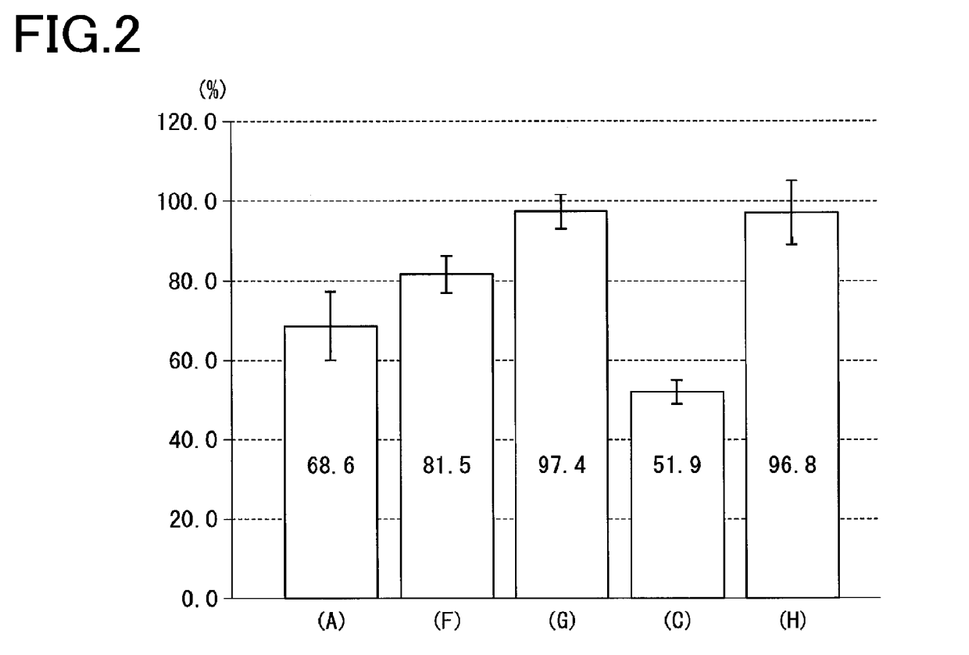
FIG. 2 is a graph showing assessment of drug sensitivity under Conditions A, C, F, G and H of Example 2.

As shown in FIG. 2, the cells to which $1 \times 10^8$ exosomes were added (Condition F) and cells to which $1 \times 10^9$ exosomes were added (Condition G) had predominantly higher CNT % and higher viable count than the cells to which 0 exosomes (Condition A) were added (cells having no addition of the exosomes derived from a drug resistant cell line), thus indicating acquisition of drug resistance. Further, the cells to which $1 \times 10^8$ exosomes were added (Condition F) and cells to which $1 \times 10^9$ exosomes were added (Condition G) had results substantially similar to those of the cells to which the biological sample (A549) exhibiting drug resistance (Condition H) was added.

<Example 3> Preparation of Resistant Lines Using Extracellular Secreted Membrane Vesicles Derived from Resistant Cell Line (3)

A human lung cancer cell line A549 (ATCC No.: CCL-185) exhibiting resistance to Gefitinib (Iressa tablets 250 manufactured by AstraZeneca) was used as a biological sample exhibiting drug resistance, and a human lung cancer cell line NCI-H1975 (ATCC No.: CRL-5908) was used as cells exhibiting no drug resistance.

As a cell culture vessel, a Transwell cell culture insert (#3470 manufactured by Corning Incorporated) was used. The culture medium used was D-MEM (043-30085 manufactured by Wako Pure Chemical Corporation) containing 10 vol/vol % of bovine serum (EXO-FBS-50A-1 manufactured by System Biosciences, LLC), and 1 vol/vol % of penicillin-streptomycin (168-23191 manufactured by Wako Pure Chemical Corporation).

Cells exhibiting no drug resistance were subjected to fluorescent labeling (PKH67GL manufactured by SIGMA Corporation) in advance, and drug sensitivity was assessed through viable count analysis.

Drugs were each assessed three times using a final concentration of 10 μM of Gefitinib.

As exosomes derived from drug resistant cell line, ones recovered from the culture supernatant of human lung cancer cell line A549 (ATCC No.: CCL-185)) by ultracentrifugation were used. Assessments were conducted with respect to two conditions of 0 exosomes (no addition of the exosomes derived from the drug resistant cell line), and $1 \times 10^9$ exosomes.

In viable count analysis, drug sensitivity was assessed, as in Example 1, by using a trypan blue solution and by counting cells in the fluorescence mode of a cell counter (Countess II) manufactured by Life Technologies Inc.

In the drug sensitivity assessment,CNT(cell viability) %=(viable count with addition of drug)/(viable count with addition of no drug)×100(%) was used as an assessment value.

As a reference, cells with an addition of $1 \times 10^9$ exosomes derived from the serum of a healthy person were also assessed.

The detailed procedure is as shown below.

<1> Seeding and Culturing of Cell Line Exhibiting No Drug Resistance (1) $2 \times 10^4$ NCI-H1975 cells were seeded in a Transwell cell culture insert.

(2) An appropriate amount of culture medium was added to the Transwell cell culture insert, followed by culturing in a $CO_2$ incubator (37° C., 5% $CO_2$) for 24 hours.

<2> Co-Culturing of Exosomes (1) An appropriate amount of culture medium was mixed with exosomes to prepare exosome medium solutions containing 0 exosomes (no addition of exosomes derived from a drug resistant cell line) and $1 \times 10^9$ exosomes.

(2) Each solution was added to the Transwell cell culture insert, followed by culturing in a $CO_2$ incubator (37° C., 5% $CO_2$) for 24 hours.

<3> Addition of Drug (1) An appropriate amount of the culture medium was mixed with a drug so as to have a final concentration of 10 μg/mL.

(2) The mixture was added to the Transwell cell culture insert, followed by culturing in a $CO_2$ incubator (37° C., 5% $CO_2$) for 72 hours.

<4> Drug Sensitivity Assessment

In viable count analysis, drug sensitivity was assessed, as in Example 1, by using a trypan blue solution and by counting cells in the fluorescence mode of a cell counter (Countess II) manufactured by Life Technologies Inc.

In the drug sensitivity assessment,CNT(cell viability) %=(viable count with addition of drug)/(viable count with addition of no drug)×100(%) was used as an assessment value.

TABLE 1

| Drug | | CNT (%) | |
|---|---|---|---|
| Gefitinib | Exosomes | Average value | S.D. |
| 10 µM | 0 | 59.9 | 5.7 |
| 10 µM | $1 \times 10^9$ derived from A549 | 89.2 | 13.6 |
| 10 µM | $1 \times 10^9$ derived from serum of healthy person | 57.7 | 2.7 |

As shown in Table 1, the cells to which $1 \times 10^9$ exosomes were added had predominantly higher CNT than the cells with no addition of exosomes derived from a drug resistant cell line (the sample of 0 exosomes in Table 1), thus indicating acquisition of drug resistance.

When the exosomes derived from the serum of a healthy person were used, CNT was substantially the same as that of the 0-exosome sample.

<Example 4> Preparation of the Resistant Lines Using the Exosomes Derived from a Patient Exhibiting Resistance As a biological sample exhibiting drug resistance, exosomes derived from patient serum exhibiting resistance to Cetuximab (Erbitux manufactured by Merck Serono) were used. As cells exhibiting no drug resistance, human colorectal cancer cell line NCI-H508 (ATCC No.: CCL-253) was used.

As a cell culture vessel, a Transwell cell culture insert (#3470 manufactured by Corning Incorporated) was used. The culture medium used was D-MEM (043-30085 manufactured by Wako Pure Chemical Corporation) containing 10 vol/vol % of bovine serum (EXO-FBS-50A-1 manufactured by System Biosciences, LLC), and 1 vol/vol % of penicillin-streptomycin (168-23191 manufactured by Wako Pure Chemical Corporation).

Cells exhibiting no drug resistance were subjected to fluorescent labeling (PKH67GL manufactured by SIGMA Corporation) in advance, and drug sensitivity was assessed through viable count analysis.

Drugs were each assessed three times using final concentrations of 0.01 µg/mL and 0.1 µg/mL of Cetuximab.

The exosomes used were recovered from patient serum R11 (exosomes derived from patient serum exhibiting resistance to Cetuximab) by ultracentrifugation. Assessments were conducted for three conditions, i.e., equivalent to 0-µL serum (no addition of exosomes derived from serum), equivalent to 9-µL serum (addition of exosomes equivalent to 9-µL serum), and equivalent to 45-µL serum (addition of exosomes equivalent to 45-µL serum).

In viable count analysis, drug sensitivity was assessed, as in Example 1, by using a trypan blue solution and by counting cells in the fluorescence mode of a cell counter (Countess II) manufactured by Life Technologies Inc.

In the drug sensitivity assessment, CNT(cell viability)
%=(viable count with addition of drug)/(viable count with addition of no drug)×100(%) was used as an assessment value.

As a reference, cells with an addition of exosomes derived from patient serum exhibiting no resistance were also assessed.

The detailed procedure is as shown below.

<1> Seeding and Culturing of Cell Line Exhibiting No Drug Resistance (1) $2 \times 10^4$ NCI-H508 cells were seeded in a Transwell cell culture insert.

(2) An appropriate amount of culture medium was added to the Transwell cell culture insert, followed by culturing in a $CO_2$ incubator (37° C., 5% $CO_2$) for 24 hours.

<2> Co-Culturing of Exosomes (1) An appropriate amount of culture medium was mixed with exosomes to prepare exosome medium solutions containing exosomes equivalent to 0-µL serum (no addition of exosomes derived from serum), equivalent to 9-µL serum, and equivalent to 45-µL serum.

(2) Each solution was added to the Transwell cell culture insert, followed by culturing in a $CO_2$ incubator (37° C., 5% $CO_2$) for 6 hours.

<3> Addition of Drug (1) An appropriate amount of culture medium was mixed with a drug so as to have final concentrations of 0.01 µg/mL and 0.1 µg/mL.

(2) The mixture was added to the Transwell cell culture insert, followed by culturing in a $CO_2$ incubator (37° C., 5% $CO_2$) for 72 hours.

<4> Drug Sensitivity Assessment

In viable count analysis, drug sensitivity was assessed, as in Example 1, by using a trypan blue solution and by counting cells in the fluorescence mode of a cell counter (Countess II) manufactured by Life Technologies Inc.

In the drug sensitivity assessment, CNT(cell viability)
%=(viable count with addition of drug)/(viable count with addition of no drug)×100(%) was used as an assessment value.

TABLE 2

| Drug | | CNT (%) | |
|---|---|---|---|
| Cetuximab | Exosomes | Average value | S.D. |
| 0.01 µg/mL | Equivalent to 0-µL serum derived from patient exhibiting resistance | 53.6 | 5.3 |
| 0.01 µg/mL | Equivalent to 9-µL serum derived from patient exhibiting resistance | 54.8 | 4.1 |
| 0.01 µg/mL | Equivalent to 45-µL serum derived from patient exhibiting resistance | 78.6 | 6.4 |
| 0.01 µg/mL | Equivalent to 45-µL serum derived from patient exhibiting no resistance | 61.9 | 6.4 |
| 0.1 µg/mL | Equivalent to 0-µL serum derived from patient exhibiting resistance | 38.4 | 4.5 |
| 0.1 µg/mL | Equivalent to 9-µL serum derived from patient exhibiting resistance | 35.5 | 4.1 |
| 0.1 µg/mL | Equivalent to 45-µL serum derived from patient exhibiting resistance | 56.0 | 6.8 |
| 0.1 µg/mL | Equivalent to 45-µL serum derived from patient exhibiting no resistance | 41.7 | 2.9 |

As shown in Table 2, the cells with the addition of exosomes equivalent to 9-µL serum derived from a patient exhibiting resistance showed CNT % that was almost the same as that of the cells with no addition of exosomes derived from a patient exhibiting resistance (cells with the addition of exosomes equivalent to 0-µL serum derived from a patient exhibiting resistance). On the other hand, as shown in the table, high drug resistance was acquired in the cells with the addition of exosomes equivalent to 45-µL serum derived from a patient exhibiting resistance.

The cells with the addition of exosomes equivalent to 45-µL serum derived from a patient exhibiting resistance also showed CNT % that was almost the same as that of the cells with no addition of exosomes derived from a patient exhibiting resistance (cells with the addition of exosomes equivalent to 0-µL serum derived from a patient exhibiting resistance).

The embodiments of the present invention have so far been described. However, configurations, combinations of the configurations, and the like of the embodiments are only examples, and additions, omissions, substitutions, or any other changes in configurations may be made without departing from the spirit of the present invention. Further, the present invention should not be limited by these embodiments.

As discussed above, the present application addresses the following; the relevancy between genetic mutation and acquisition of drug resistance is that, while many related genes are being identified due to recent innovations in gene analysis technology, acquisition of drug resistance in cancer-associated genes is yet to be comprehensively uncovered.

In drug screening, it is important to assess various types of drugs by adapting them to various types of drug resistant cell groups, from the viewpoint of the comprehensive analyses. However, there have been no reports regarding a method of easily giving drug resistance to various types of cells to prepare various types of drug resistant cell groups.

In the research and development of anticancer drugs, from among many drugs, drugs have been assessed for effectiveness through a conventional assessment procedure. However, this assessment is often not consistent with the actual clinical results. Drug developers, particularly pharmaceutical companies have an enormous number of candidate drug compounds, and are seeking new assessment under study which can rescreen these candidate drug compounds, i.e., seeking drug assessment screening groups for rescreening other unprecedented adaptabilities.

The present invention in one aspect provides a method of more quickly and simply preparing cells exhibiting drug resistance, and a novel method of screening for assessing an anticancer drug more quickly and simply.

The present inventors have found that drug resistance can be acquired in cells exhibiting no drug resistance, using exosomes derived from a living organism exhibiting drug resistance, and that cancer cells which have acquired drug resistance due to the exosomes can be used for screening anticancer drugs.

A method according to a first aspect of the present invention includes preparing cells exhibiting drug resistance by bringing exosomes, which are derived from a living organism exhibiting drug resistance, into contact with cells exhibiting no drug resistance, and culturing the cells.

The cells exhibiting no drug resistance are cultured in a culture medium containing any of a body fluid sample collected from an animal exhibiting drug resistance, a cell extract collected from an animal exhibiting drug resistance, a cell culture supernatant collected from an animal exhibiting drug resistance, an extract of cultured cells exhibiting drug resistance, and a culture supernatant of cultured cells exhibiting drug resistance.

The body fluid sample may be any one of blood, serum, plasma, urine, buffy coat, saliva, semen, breast exudate, cerebrospinal fluid, tears, sputum, mucus, lymph fluid, ascites, pleural effusion, amniotic fluid, bladder lavage fluid, and bronchoalveolar lavage fluid.

Type of cells may be different between the cultured cells exhibiting drug resistance and the cells exhibiting no drug resistance.

The cultured cells exhibiting drug resistance may be any one type of cells selected from the group consisting of neuronal cells, dendritic cells, immune cells, vascular endothelial cells, lymphatic endothelial cells, fibroblast cells, epithelial cells, myocardial cells, liver cells, pancreatic islet cells, smooth muscle cells, cancer cells, and cancer stem cells.

The animal may be a human.

The exosomes are those exosomes which are collected from a cancer patient and exhibit drug resistance.

The cells exhibiting no drug resistance may be cancer cells.

A cancer from which the cancer cells are derived may be any one of metastatic medulloblastoma, gastrointestinal stromal tumor, dermatofibrosarcoma protuberans, colon cancer, rectal cancer, lung cancer, chronic myeloproliferative disease, acute myelogenous leukemia, thyroid cancer, pancreatic cancer, bladder cancer, kidney cancer, malignant melanoma, breast cancer, prostate cancer, ovarian cancer, cervical cancer, head and neck cancer, brain tumor, and liver cancer.

The exosomes may be cultured for 12 hours or more together with the cells exhibiting no drug resistance.

The number of exosomes may be $1 \times 10^3$ or more relative to $2 \times 10^4$ cells exhibiting no drug resistance.

A method of screening anticancer drugs according to a second aspect of the present invention includes: a drug resistance acquiring step of acquiring drug resistance in cancer cells exhibiting no drug resistance by the method related to the aspect set forth above; an anticancer drug addition step of, after the drug resistance acquiring step, bringing at least one type of anticancer drug into contact with the cancer cells that have acquired drug resistance; and an assessment step of, after the anticancer drug addition step, calculating viability of the cancer cells and assessing the anticancer drug.

The drug resistance may be resistance against a tyrosine kinase inhibitor or an EGFR inhibitor.

The cancer cells that have acquired the drug resistance may have 0.1% or less mutations in resistance genes which are against the tyrosine kinase inhibitor or the EGFR inhibitor.

In the drug resistance acquiring step, the cancer cells that have acquired the drug resistance may be further co-cultured with at least one other type of cells, and organized three-dimensionally.

The cells co-cultured with the cancer cells that have acquired the drug resistance may be at least one type of cells selected from the group consisting of neuronal cells, dendritic cells, immune cells, vascular endothelial cells, lymphatic endothelial cells, fibroblast cells, epithelial cells, myocardial cells, liver cells, pancreatic islet cells, smooth muscle cells, cancer cells, and cancer stem cells.

An anticancer drug screening kit according to a third aspect of the present invention includes exosomes which are derived from a living organism exhibiting drug resistance, and cancer cells exhibiting no drug resistance.

The anticancer drug screening kit may further include a cell culture vessel. In the kit, the cancer cells may be provided in the cell culture vessel.

According to the aspects of the present invention described above, there are provided a method of more quickly and simply preparing cells exhibiting drug resistance, and a method of screening for assessing the anticancer drug more quickly and simply.

INDUSTRIAL APPLICABILITY

The present invention described above can provide, in one aspect, a method of more quickly and simply preparing cells exhibiting drug resistance, and a method of screening for assessing anticancer drugs more quickly and simply. Furthermore, the cells exhibiting drug resistance obtained by the preparation method can be applied to new drug development, assessment in drug repositioning, selection and assessment of medical treatment, resolution and research for the mechanism of acquiring drug resistance, and the like.

Obviously, numerous modifications and variations of the present invention are possible in light of the above teachings. It is therefore to be understood that within the scope of the appended claims, the invention may be practiced otherwise than as specifically described herein.

What is claimed is:

1. A method of producing drug resistant cells, comprising:
preparing exosomes derived from a living organism exhibiting drug resistance;
adding the exosomes to cells exhibiting no drug resistance such that the exosomes make contact with the cells exhibiting no drug resistance and that drug resistant cells are formed from the cells exhibiting no drug resistance; and
culturing the drug resistant cells in a culture medium,
wherein the adding includes adding the exosomes to the cells exhibiting no drug resistance at a ratio such that a number of the exosomes is in a range of $1\times10^3$ to $1\times10^{12}$ with respect to $2\times10^4$ of the cells exhibiting no drug resistance.

2. The method of claim 1, further comprising:
culturing the cells exhibiting no drug resistance in a culture medium including one of a body fluid sample from an animal exhibiting drug resistance, a cell extract from an animal exhibiting drug resistance, a cell culture supernatant from an animal exhibiting drug resistance, an extract of cultured cells exhibiting drug resistance, and a culture supernatant of cultured cells exhibiting drug resistance.

3. The method of claim 2, wherein the body fluid sample is one of blood, serum, plasma, urine, buffy coat, saliva, semen, breast exudate, cerebrospinal fluid, tears, sputum, mucus, lymph fluid, ascites, pleural effusion, amniotic fluid, bladder lavage fluid, and bronchoalveolar lavage fluid.

4. The method of claim 2, wherein the cells exhibiting no drug resistance are cultured in the culture medium including one of an extract of cultured cells exhibiting drug resistance, and a culture supernatant of cultured cells exhibiting drug resistance, and the cultured cells exhibiting drug resistance are different from the cells exhibiting no drug resistance.

5. The method of claim 2, wherein the cells exhibiting no drug resistance are cultured in the culture medium including one of an extract of cultured cells exhibiting drug resistance, and a culture supernatant of cultured cells exhibiting drug resistance, and the cultured cells exhibiting drug resistance comprise at least one selected from the group consisting of neuronal cells, dendritic cells, immune cells, vascular endothelial cells, lymphatic endothelial cells, fibroblast cells, epithelial cells, myocardial cells, liver cells, pancreatic islet cells, smooth muscle cells, cancer cells, and cancer stem cells.

6. The method of claim 2, wherein the cells exhibiting no drug resistance are cultured in the culture medium including one of a body fluid sample from an animal exhibiting drug resistance, a cell extract from an animal exhibiting drug resistance, and a cell culture supernatant from an animal exhibiting drug resistance, and the animal is a human.

7. The method of claim 1, wherein the exosomes are derived from a cancer patient exhibiting drug resistance.

8. The method of claim 1, wherein the cells exhibiting no drug resistance are cancer cells.

9. The method of claim 8, wherein the cancer cells are from one of metastatic medulloblastoma, gastrointestinal stromal tumor, dermatofibrosarcoma protuberans, colon cancer, rectal cancer, lung cancer, chronic myeloproliferative disease, acute myelogenous leukemia, thyroid cancer, pancreatic cancer, bladder cancer, kidney cancer, malignant melanoma, breast cancer, prostate cancer, ovarian cancer, cervical cancer, head and neck cancer, brain tumor, and liver cancer.

10. The method of claim 1, wherein the preparing includes culturing the exosomes for 12 hours or more together with the cells exhibiting no drug resistance.

11. The method of claim 2, wherein the adding includes adding the exosomes to the cells exhibiting no drug resistance at a ratio such that a number of the exosomes is in a range of $1\times10^7$ to $1\times10^{12}$ with respect to $2\times10^4$ of the cells exhibiting no drug resistance.

12. The method of claim 1, wherein the adding includes adding the exosomes to the cells exhibiting no drug resistance at a ratio such that a number of the exosomes is in a range of $1\times10^7$ to $1\times10^{12}$ with respect to $2\times10^4$ of the cells exhibiting no drug resistance.

13. The method of claim 1, wherein the culturing includes culturing the drug resistant cells in the culture medium such that a cell viability, CNT, is at least 80% when a drug sensitivity is accessed based on the cell viability.

* * * * *